United States Patent [19]

Hellstrom

[11] 4,158,138
[45] Jun. 12, 1979

[54] MICROPROCESSOR CONTROLLED X-RAY GENERATOR

[75] Inventor: Melbourne J. Hellstrom, Severna Park, Md.

[73] Assignee: CGR Medical Corporation, Baltimore, Md.

[21] Appl. No.: 845,138

[22] Filed: Oct. 25, 1977

[51] Int. Cl.² .............................................. H05G 1/46
[52] U.S. Cl. ................................... 250/402; 250/406; 250/408
[58] Field of Search ............... 250/402, 416, 413, 415, 250/322, 401; 364/414, 415

[56] References Cited

U.S. PATENT DOCUMENTS

| 3,916,192 | 10/1975 | Schmitmann et al. | 250/322 |
| 4,035,648 | 7/1977 | Patel | 250/402 |

FOREIGN PATENT DOCUMENTS 2318367  10/1974  Fed. Rep. of Germany ........... 250/402

OTHER PUBLICATIONS

Schmitmann et al., "Tridoros Optimatic — a New Generator System," *Electromedica*, 1971, pp. 83–86.

Primary Examiner—Alfred E. Smith
Assistant Examiner—T. N. Grigsby
Attorney, Agent, or Firm—Brady, O'Boyle & Gates

[57] ABSTRACT

A diagnostic X-ray system operative in response to control signals from a stored program digital computer to generate an X-ray beam and to produce an image of the object through which the X-ray beam passes. The computer which is preferably a microprocessor has a plurality of selectable programs stored in a digital memory and is operable to control a plurality of operations such as maximizing image quality in terms of resolution, verifying the available anode heat capacity, providing the necessary wait time between successive exposures in a tomographic series, storing the X-ray tube(s) histories, storing and recalling X-ray factors on an anatomic basis and, among other things, making a calculation and display of a pseudo-dose.

15 Claims, 11 Drawing Figures

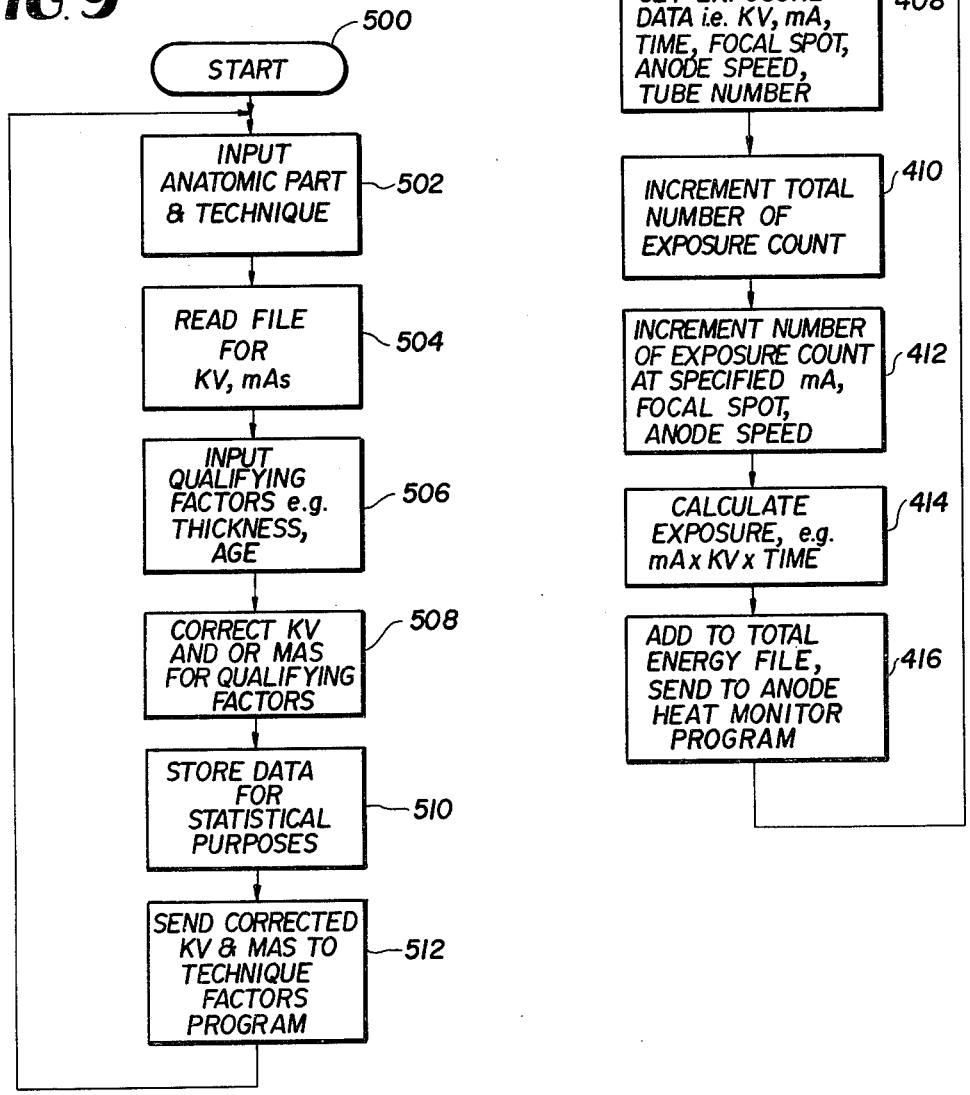

MICROPROCESSOR CONTROLLED X-RAY GENERATOR

BACKGROUND OF THE INVENTION

This invention relates to diagnostic X-ray systems and more particularly to a system controlled in accordance with a digital computer having a plurality of selectable program instruction sets for completely controlling the operation of the system consistent with a particular inputted technique or procedure, operator inputs, inherent physical limitations of associated equipment, and various safety and legislated restrictions. It is a primary object of the present invention to provide a completely automated system of X-ray control whereby exposure optimization is effected in a sense of image quality, in particular resolution, and to maximize X-ray tube life.

X-ray tubes today are generally provided with two focal spot sizes, small and large, and are adapted to operate at two speeds, standard speed and ultra speed. It is also well known that X-ray image resolution is higher when the focal spot is smaller. Another thing which is known to effect image resolution is motion of the patient, either voluntary or involuntary, which causes blurring of the image. Examples of involuntary motion are those due to respiration, to the cardiovascular system, and to the digestive system. In order to minimize the deleterious effects of this type of motion on image quality, an attempt is made to keep the X-ray exposure time as small as possible. This, however, runs into conflict with the capability of the X-ray tube to withstand the relatively large amounts of heat dissipated. Generally this X-ray tube capability is expressed in the form of tube loading charts which are supplied by the X-ray tube manufacturer. In order to get the proper exposure of an X-ray film, the X-ray technique factors are selected largely by experience, but from a technical point of view in accordance with two rough guidelines. The first is the kilovoltage (kV) which has to be high enough to penetrate the subject, i.e. the photon energy must be high enough so that sufficient photons can exit from the patient in spite of absorption. Second the product of current expressed in milliamperes (mA) and time (s) expressed in seconds must be chosen long enough so that there is a sufficient number of photons passing through the patient in order to darken the film. As a rough guideline, film darkening is proportional to the product of $mAs \times kV^n$ where n, for example, equals 4.

The following listing comprises prior art of which the applicant is aware:
U.S. Pat. No. 4,035,648, Patel
U.S. Pat. No. 3,997,791, Winkler
U.S. Pat. No. 3,917,949, Winkler
U.S. Pat. No. 3,746,862, Lombardo, et al.
U.S. Pat. No. 3,838,285, Siedband, et al.
U.S. Pat. No. 3,968,372, Laughinghouse

SUMMARY

Accordingly, the present invention is directed to a control system for X-ray generator apparatus operable in accordance with a plurality of selectable instruction programs stored in the digital memory of a microprocessor. One such program operates to maximize image quality in terms of resolution while at the same time maximizing X-ray tube life. Accordingly, the operator inputs the values of mA, time expressed as s, and kV or of mAs and kV which have been selected by the operator for the diagnostic procedure, or which may come from a predetermined table of values, e.g. an "anatomic table" in which case the operator chooses such diagnostic examination related parameters such as that portion of the human anatomy to be X-rayed, the view, and the patient thickness. The memory outputs an instruction program whereupon the largest value of mA available from the generator is used to calculate the corresponding minimum possible value of exposure time expressed as s by dividing this maximum mA value into the selected value of the mA $\times$ s, i.e. mAs. Having calculated the minimum possible time, these values are compared with selected one of a plurality of tube loading chart characteristic curves which have been digitally stored in the memory. The first choice of curves, for example, is the small focal spot, standard speed curve. Upon comparison, if the inputted factors are consistent, i.e. do not exceed the permissible dissipation with the tube loading chart curve selected, i.e. the exposure is permissible, then the computer initiates the necessary steps to permit exposure. If on the other hand the tube loading chart is exceeded, the program effects a shift in technique factors, for example a decrease in mA, while keeping the mAs product a constant, which results in a corresponding increase in exposure time. The new shifted technique factors again are compared with the two selected tube charts to see whether or not an exposure can now be made. If the exposure still cannot be made the process is again repeated. The process of reducing mA and increasing time, while it reduces power dissipation and therefore increases the possibility of satisfying the requirements of the tube rating charts, does increase the exposure time. This, however, causes a deleterious effect on image resolution as it relates to motion blurring. Consequently, each time a "constant mAs shift" as defined above is made, the resulting exposure time is compared to a predetermined value which has been selected by the operator as the maximum permissible from the point of view of tolerable motion blurring. If the calculated time exceeds this predetermined value, then either that set of factors or the next one which would be obtained by another constant mAs shift is not permissible. Once this condition is reached it is possible to reduce power dissipation in the anode by increasing the kV and decreasing the mA. This is done in such a way that the film darkening factor of the exposure is kept constant. Since mA will decrease faster than kV increases, the net result is a reduction in power dissipated in the X-ray tube and an exposure may be possible for that set of tube conditions, i.e. focal spot and anode speed. This shift is defined as the "kV shift". As with the "constant mAs shift", there is a practical limit to the permissible "kV shift" which is based on radiation physics. If the combination of constant mAs and kV shifts does not come up with a set of factors which will permit an exposure with the tube loading charts of first choice, then the computer program moves to the next most desirable tube chart, e.g. small focal spot, ultra speed whereupon the testing process is repeated again starting with the original factors inputted by the operator. Successively then, all of the possible tube charts for the tube(s) operating modes are stepped through in the order of desirability, based on considerations of image quality and tube life, until either an allowable set of exposure factors is found, or it is determined that no exposure is possible within the constraints of the program. Additional functions are also provided by respective programs such as the verification of the available anode heat capacity, the necessary wait time between successive exposures in a tomographic series, the storge of X-ray tube history, the storage of X-ray factors and their recall on an anatomic basis, and the recording of estimated patient dosage.

DESCRIPTION OF THE DRAWINGS

FIGS. 5 through 11 set forth illustrate flow charts indicative of a plurality of selectable instruction programs stored in the computer's memory for controlling the system as shown in FIG. 4.

DETAILED DESCRIPTION OF THE PREFERRED EMBODIMENT

Figure 1:
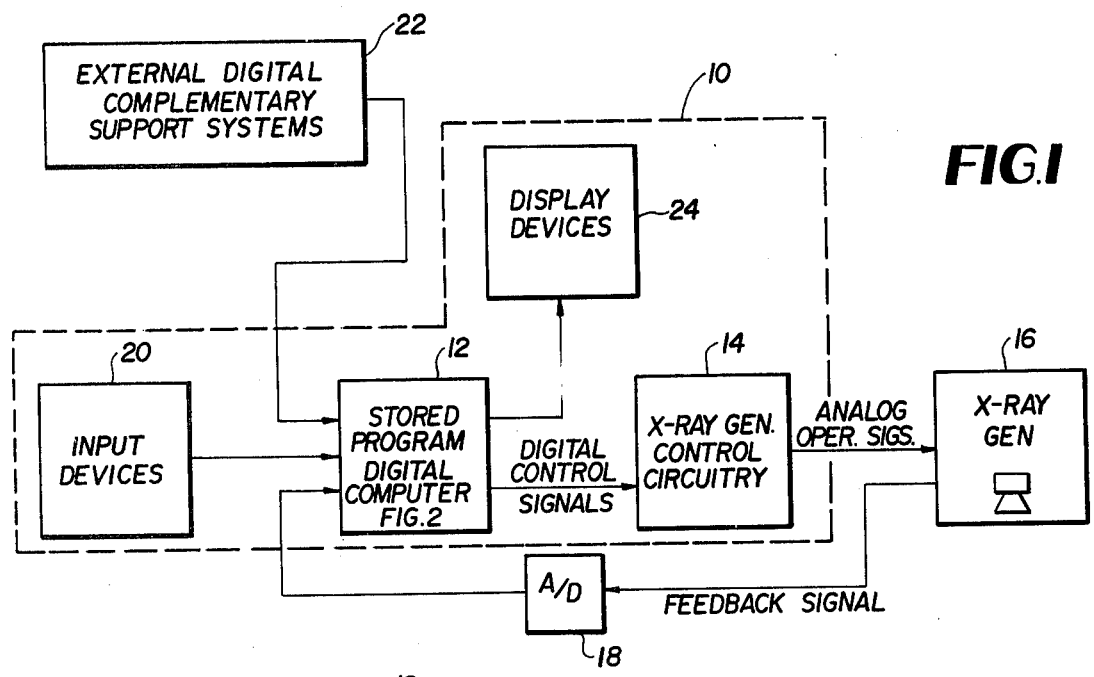
FIG. 1 is a block diagram outlining the broad features of the subject invention.

Prior to discussing the details of the invention, the following general considerations relating to a typical digital computer are offered by way of background. Typically, a digital computer consists of three main elements, (a) a central processor unit (CPU), (b) a memory, and (c) a plurality of input/output ports. The memory serves as a place to store instructions and data, the instructions being coded pieces of information that direct the activities of the CPU and the data being the coded pieces of information that are processed by the CPU. A group of logically related instructions stored in memory is referred to as a program. The CPU accordingly "reads" each instruction from memory in a logically determined sequence and uses it to initiate processing actions. If the instruction sequence is coherent and logical, processing the program will produce intelligible and desired results.

As noted above, the memory is also used to store the data to be manipulated as well as instructions that direct the manipulation. The program must be organized such that the CPU does not read a non-instruction word when it expects to see an instruction. The CPU can rapidly access any data stored in memory, and includes temporary storage registers of its own, but often the data required for processing is not known in advance, or cannot be derived from existing information. This problem is resolved by providing the computer with one or more input/output ports. The CPU then addresses these ports and inputs or outputs the data from or to the external devices coupled thereto. An alternate method of communicating to external devices is to associate each device with a unique address thereby permitting the CPU to treat the devices as memory locations. The output, for example, may go to a display for use by a human operator or to a peripheral device such as a line printer, to a storage device or the output may constitute process control signals that direct the operations of another system, which in the subject invention comprises radiological apparatus. The input and output ports together permit the CPU and memory to communicate with the outside world.

Bearing the foregoing in mind, the inventive concept of the present invention is directed to a system of computerized control of an X-ray generator system to simplify the steps taken by an X-ray technologist in making a radiological examination. Of primary interest, however, is to provide the best possible image in terms of resolution while at the same time minimizing ultra speed usage of the X-ray tube since such usage tends to reduce bearing life, for example, due to the fact that natural resonances of the anode tube structure may be encountered on the way up to and down from ultra speed operation and heat dissipation in the motor structure is greater at ultra speed.

Three objectives evolve from this requirement. First of all, it is desirable to use the X-ray tube or tubes under focal spot and anode speed conditions in some order or priority. For example: (a) small focal spot, standard speed; (b) small focal spot, ultra speed; (c) large focal spot, standard speed; and finally, (d) large focal spot, ultra speed, are preferable to emphasize high resolution images. Secondly, intrinsic in the technique factors selected by the operator, whether it be the three parameters of voltage (kV), current (mA), and time (s) or simply kV and mAs or "anatomic" which is a set of preselected parameters depending upon the part of the anatomy to be X-rayed and the type of examination performed as well as some indication of the patient's physical specifications, there is a quantity called the "film darkening factor" (FDF) which must be taken into account. Film darkening factor is proportional to the product of current, time and voltage, and more particularly, $$\text{FDF} \propto (\text{mA}) \times (\text{time}) \times (\text{kV})^n,$$

where n is on the order of 4 or 5. While the requested technique factors may change, it is nevertheless desirable from the point of view of an acceptably exposed film that the value of the film darkening factor be kept substantially constant. And thirdly, it is desirable to utilize the minimum possible exposure time for a set of operating conditions in order to avoid motion blurring.

It should be pointed out, however, that the first and third of the above three objectives are incompatible since for a given mAs a shorter exposure time results in a higher mA and this may, at some fixed kV, mandate the use of a large focal spot because of high power dissipation in the anode of the X-ray tube.

Considering now the drawings, reference is now made to FIG. 1, which exemplifies the subject invention in its broadest aspects. Reference numeral 10 designates a digitally controlled diagnostic X-ray system including a stored program digital computer 12, which is adapted to feed digital control signals to X-ray generator control circuitry 14 which responds to digital control signals to develop analog operational control signals which are fed to X-ray generator apparatus 16 located in a radiological examination room which, for example, consists of a high voltage transformer rectifier assembly connected to one or more X-ray tubes. Actually the partitioning between the analog control circuits 14 and the X-ray generator 16 is somewhat arbitrary being physically determined by commercial manufacturing and technical reasons. It is conceivable, for example, that elements 14 and 16 be physically contained in the same cabinet, or in separate cabinets in the same room. The apparatus 16 additionally develops necessary feedback signals which are coupled back to the stored program digital computer 12 by means of analog to digital converter means 18. Input devices 20 consisting of keyboards, pushbuttons, switches, and other devices for inputting, for example, technique factors, e.g. mA, kV and time as well as radiological procedure selection one typical example of which is tomography, are adapted to couple input signals to the stored program digital computer 12 along with other desired digital input signals from, among other things, external digital complementary support systems 22. Such support systems may, for example, consist of computer assisted hospital or radiology department data systems currently being utilized for purposes such as patient registration, scheduling, record keeping and accounting in hospitals. Additionally, the computer 12 is coupled to suitable display and readout devices 24 consisting of, for example, cathode ray tubes, LED alpha numeric displays, printers, loud speakers, etc. which are both necessary and desirable for advising the operator or other personnel of information relative to system operation.

The stored program digital computer 12 preferably comprises a microprocessor having a plurality of instruction programs stored in a digital memory such as a ROM or PROM fabricated on a semiconductor chip. Such devices are currently available as off-the-shelf items, and when combined with the subject X-ray generator system, the system is adapted to completely handle all control functions once operator selected inputs or other inputs from external support systems are coupled to the computer's input ports. The microprocessor embodiment of the stored program digital computer 12 is shown in greater detail in FIG. 2 and comprises an integrated circuit central processing unit (CPU) 26, a typical example being an Intel Corp. 8080 eight-bit parallel control processor unit fabricated on a single LSI chip. The CPU 26 couples to an address bus 28 which comprises a sixteen-bit three state address bus as well as an eight-bit, bi-directional three state data bus 30. Additionally, a control bus 32 is included which is adapted, for example, to handle six timing and control outputs, four control inputs, four power inputs and two clock inputs. In addition to the 8080 CPU 26, the microprocessor digital computer 12 includes a digital memory 34 consisting of, for example, one or more Intel 2708 programmable read only memory chips (PROM) 34A and one or more Intel 2701 read/write random access memory chips (RAM) 34B which are readily adaptable to be mated with an 8080 CPU. The PROM 34A is coupled to the address, data and control buses 28, 30 and 32, and is adapted to store, for example, up to 1024 eight-bit instruction words in the case of the 2708 upon being programmed in a manner well known to those skilled in the art. The RAM 34B typically a 2107 device, has capacity for random access read/write storage of 512 words. Additionally, one or more input and output ports shown generally by reference numeral 36, are coupled to the address, data and control buses 28, 30 and 32.

Figure 2:
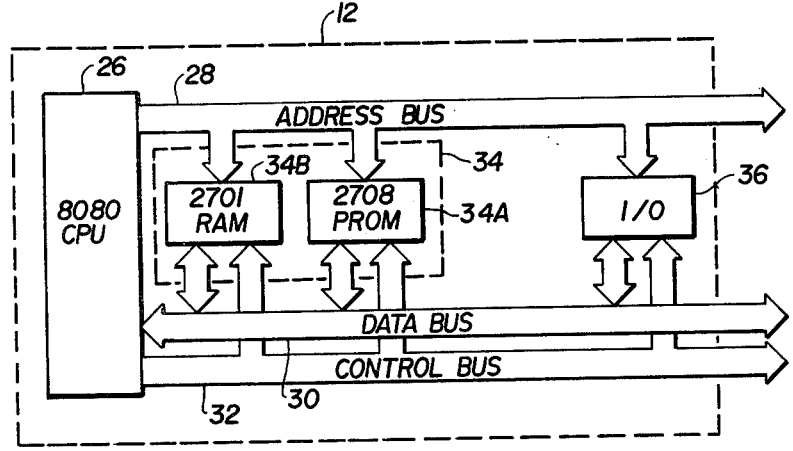
FIG. 2 is a block diagram illustrative of the essential elements of a stored program digital computer.
Figure 3:
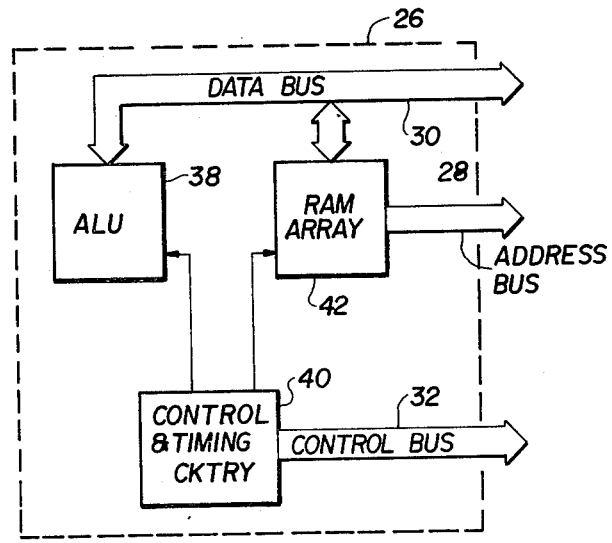
FIG. 3 is a block diagram broadly illustrative of the essential elements of a central processor unit of a digital computer.

Referring to FIG. 3, what is disclosed therein is the three functional units contained in a typical central processor unit such as the 8080 CPU 26 shown in FIG. 2. As shown, it consists of an arithmetic/logic unit (ALU) 38, timing and control circuitry 40, and a local random access memory (RAM) 42 consisting of an array of storage registers. Such an array is well known, and normally includes, inter alia, an accumulator register which stores one of the operands to be manipulated by the ALU, a program counter, an instruction register and decoder, as well as an address register.

The ALU 38 is that portion of the central processing unit hardware which as its name implies, performs the arithmetic logic operations on the binary data applied thereto. Although not shown, the ALU also contains an adder which is capable of combining the contents of two registers in accordance with the logic of binary arithmetic. This provision permits the processor to perform arithmetic manipulations on the data it obtains from memory 34, and its other inputs. The control and timing circuit 40 is the primary functional unit within the CPU for maintaining the proper sequence of events required for the desired processing task. After an instruction is fetched and decoded, the control circuitry uses the appropriate signals for initiating the proper processing action, which leads ultimately, in this case, to the control of an X-ray generator system in a predetermined manner.

Figure 4:
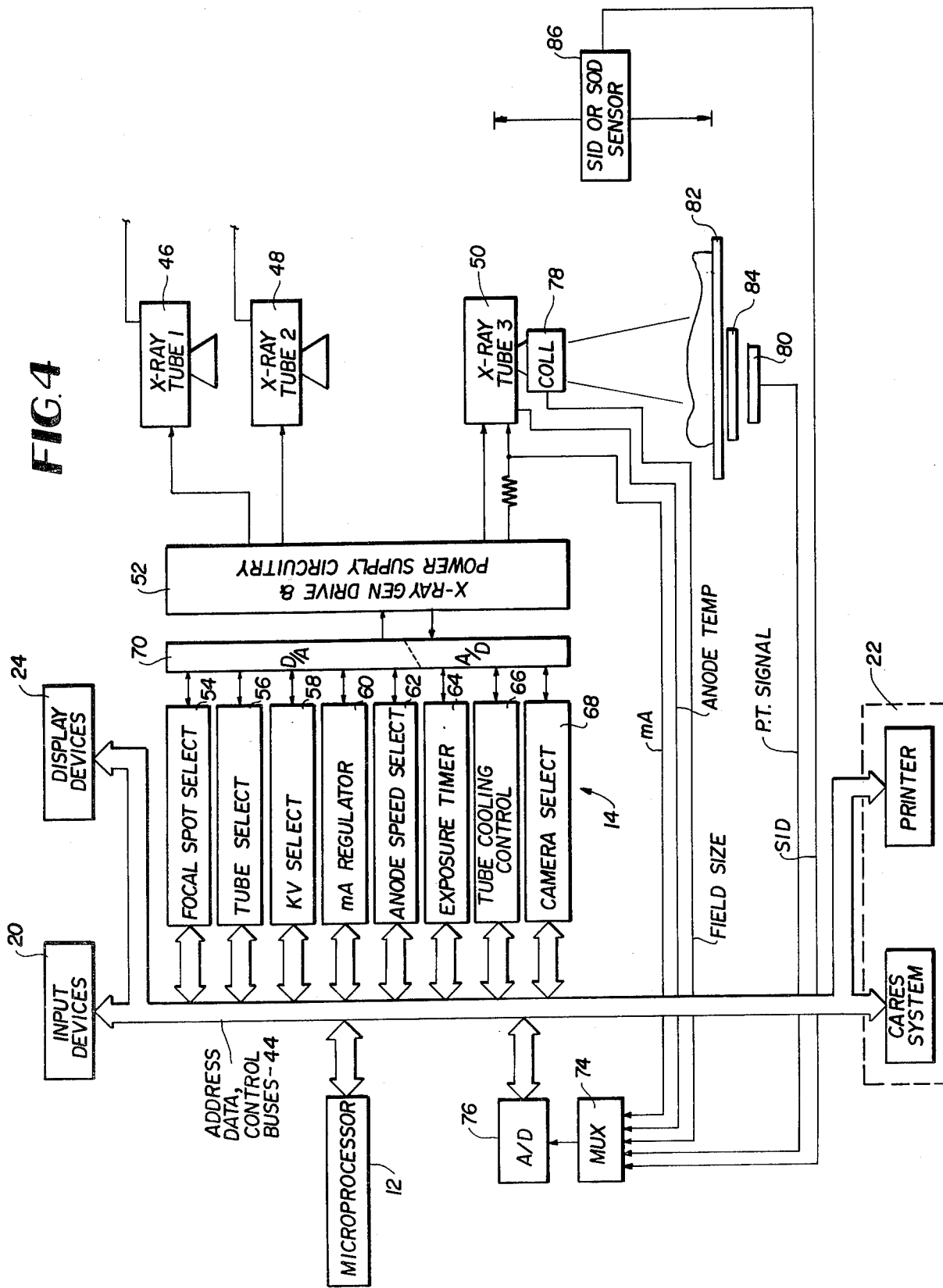
FIG. 4 is a system block diagram illustrative of the preferred embodiment of the subject invention.

With this in mind, reference is now made to FIG. 4, where there is disclosed a more detailed block diagram of the subject invention as outlined in FIG. 1. Reference numeral 44 represents the three buses 28, 30 and 32 shown in FIGS. 2 and 3 and digitally links the stored program computer, i.e. microprocessor 12 to a diagnostic X-ray generator system having for example, three X-ray tubes 46, 48 and 50 to a plurality of interface circuits 14 which are responsive to digital signals from the microprocessor 12 and are adapted to provide required analog control signals to, and to react with analog and/or digital representations of feedback signals from the drive and power supply circuitry 52 which is adapted to provide functions found in all diagnostic X-ray systems having a plurality of selectable techniques or procedural modes available to the operator. While not meant to be interpreted in a limiting sense, the interface circuits include, for example, a focal spot select circuit 54, a tube select circuit 56, a kV select circuit 58, a mA select and regulator circuit 60, an anode speed select and control and timing logic circuit 62, an exposure timer circuit 64, a tube cooling control circuit 66, and a photo or cine camera select circuit 68. Whereas all of these circuits accept digital inputs, they are coupled to the drive and power supply circuitry 52 through suitable digital to analog or analog to digital conversion circuitry 70.

In addition to the digital control signals coupled to the circuits 54 through 68 from the microprocessor computer 12, one or more other feedback signals such as X-ray tube current (mA) developed across a drop wire resistor 72, for instance, is coupled back to the buses 44 through, for example, a multiplexer or MUX 74 and an analog to digital (A/D) converter 76. Additionally, other signals such as anode temperature, field size, taken from the X-ray tube 50 and its associated collimator 78 are also fed back, for example, through the multiplexer 74 to the A/D converter 76. Also, FIG. 4 schematically discloses a photo pick-up device 80 located beneath the X-ray table 82 in the vicinity of the image receptor 84. The signal from the device 80 plus the signal from a source image distance or a source object distance sensor 86 are also coupled back to the buses 44 through, for example, the multiplexer 74 and the A/D converter 76.

It can be seen, therefore, that digital control of the X-ray system is adapted to be accomplished by the various control interface circuits 14 and appropriate feedback signals being fed back to the microprocessor computer 12 along the address, data and control buses in accordance with an instruction program stored in the digital memory 34 shown in FIG. 2.

FIGS. 5 through 11 illustrate in flow sheet format a plurality of algorithms for stored program operation of the X-ray system shown in FIG. 4. The operation indicated by the algorithms is accomplished within the microprocessor 12 in response to programming instructions previously set into the PROM 34 shown in FIG. 2. Each step or decision indicated in these flow charts may in actual implementation involve one or more step or decision, each step occasionally being an entire sub-routine by itself. The programming of these steps, however, is within the skill of the average programmer and to eliminate added complexity, they will not be dealt with. Also, in order to perform each step or decision, particularly where mechanical sequence is necessitated, an amount of time must elapse before other steps are activated. Accordingly, and where necessary, such delays must be built into the step-by-step operation indicated by the algorithm, these also being within the skill of one skilled in the art.

Figure 5:
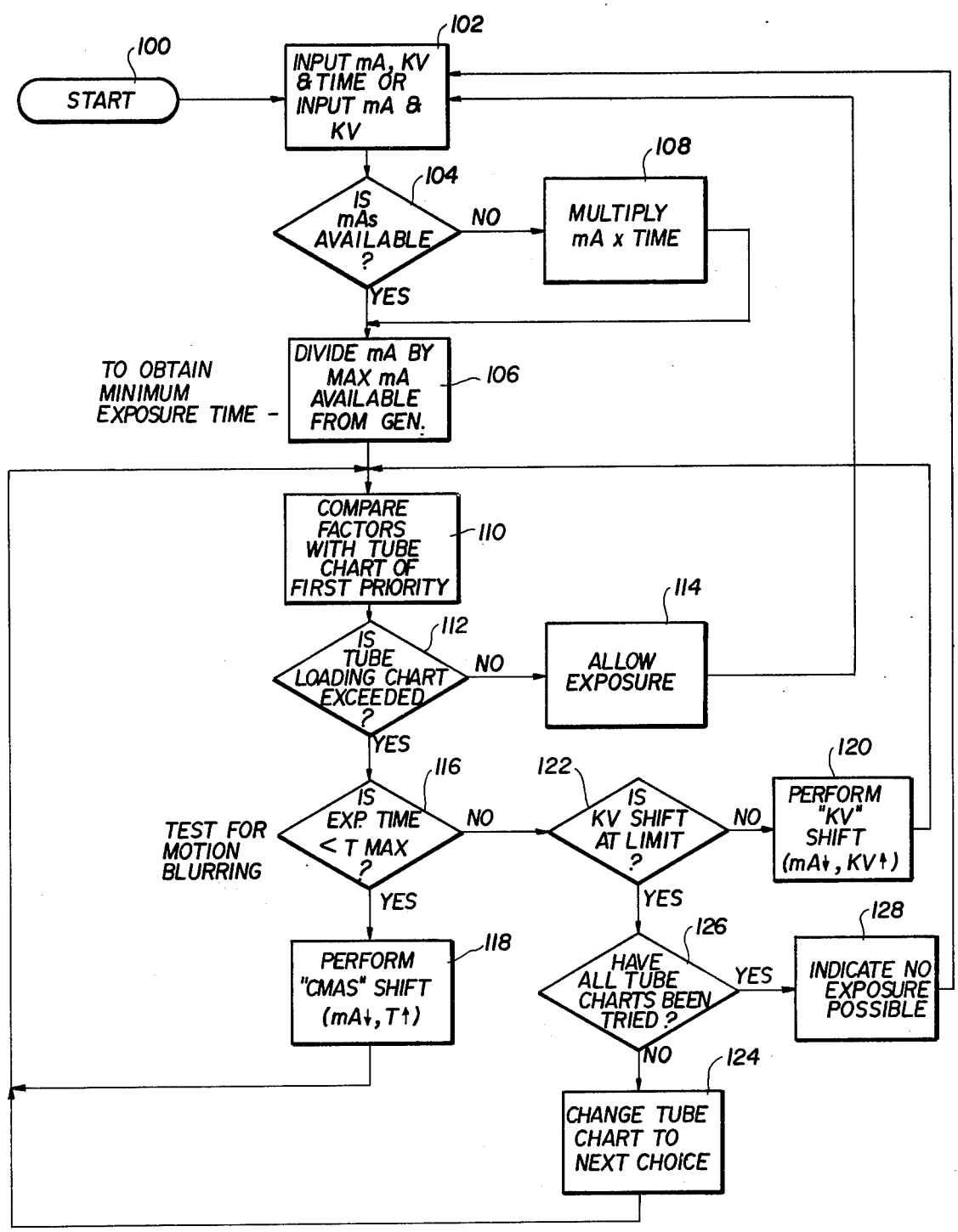

Referring now to the flow chart shown in FIG. 5, there is disclosed the procedural steps in an algorithm for accomplishing the primary object of the present invention, which is to optimize the procedure in making an X-ray exposure in the sense of image quality, in particular resolution and at the same time to maximize X-ray tube life. The algorithm set forth in FIG. 5 is based upon the aforementioned three objectives of: (1) the desirability of using the X-ray tube under focal spot and anode speed condition in a predetermined order of priority; (2) it is desirable to maintain a substantially constant film darkening factor (FDF) while shifting the technique factors of mA, time and kV in a predetermined manner until a suitable allowable tube rating chart condition is met and then permit an exposure to be made; and (3) to use the minimum exposure time possible in order to eliminate object motion blurring.

The flow chart shown in FIG. 5 indicates that following a START step 100, operator or "anatomic table" selected values of kV, mA and time or mAs and kV are inputted to the microprocessor in step 102. The processor performs a decision step 104 to establish whether or not a value of mAs i.e. current × time has been inputted and is available. If the decision is affirmative, step 106 is resorted to, however, if the decision is negative, a step 108 is performed, whereby the inputted values of mA and time are multiplied together and then step 106 is initiated. The step 106 involves a calculation in which the mAs value is divided by the maximum mA station or value available in the X-ray generator system which calculation yields the minimum exposure time possible for the mAs value selected. The tube rating chart curves for the system's X-ray tube(s) have been programmed into the PROM 34 in a well known manner, e.g. that described in U.S. Pat. No. 4,035,648 entitled "X-Ray Tube Protection Circuit", A. T. Patel. This minimum possible exposure time together with the assumed maximum mA and inputted kV are compared in step 110 with the tube rating chart of first priority, for example, the small focal spot, standard speed tube rating chart. Step 112 indicates that if the tube rating chart is not exceeded, a step 114 permitting exposure is initiated. If the tube rating chart is exceeded, however, the decision is affirmative for step 112. Accordingly, an attempt to use the mode of first priority, e.g. the small focal spot, standard speed mode of operation, is again attempted but by modifying the technique factors of mA, kV and time in two different types of factor shifting formats. However, prior to any further steps being performed, a decision step 116 is made to determine if the previously calculated exposure time is less than some predetermined amount, i.e. the maximum exposure time which is permissible in order to minimize motion blurring. This predetermined time may be different for different diagnostic procedures and patients and may be accordingly programmable by the user. If the results of the decision step 116 indicates that the time is less than this maximum exposure time, a "CMAS shift", i.e. a constant mAs shift step 118 is entered into wherein the processor causes the mA to be decreased and the time increased proportionately while keeping the mAs product constant. In an X-ray generator system where discrete mA stations are provided, the processor commands the selection of the next lower mA station and then commands the selection of a longer exposure time to keep the mAs figure constant. This can be done exactly if time is continuously variable as is possible with conventional digital circuitry; however, if time stations are discrete, then it can only be done approximately. However, if the following special provision is made in selecting the discrete mA stations of a generator and the discrete time stations of a generator, then the mAs value can be maintained constant even in the case of an X-ray generator with discrete mA and time stations. This can be accomplished by making the consecutive mA stations separated by a fixed percentage e.g. "%ΔmA" and by making consecutive time stations separated by a fixed percentage also, e.g. %ΔT and then integrally relating the two, i.e., by making $$(\%\Delta mA)/(T\Delta T) = N,$$

where N is an integer 1, 2, 3...

The system having gone to a lower mA and a longer exposure time by virtue of a CMAS shift, reverts back to step 110 and 112 to see if exposure is possible for this set of parameters in the mode of first priority, e.g., small focal spot, standard speed operation. If this is still not possible, the mA downshift step 118 is again performed as long as predetermined maximum exposure time limit for motion blurring has not yet been exceeded. Once this maximum exposure time limit is reached, then the mAs downshifting of step 118 is abandoned. Instead, a second type of technique factor shifting step 120 is performed wherein the mA value is shifted to the next lower station while time is held constant, since it has exceeded the motion blurring time limit. However, to keep the film darkening factor unchanged, the kV is increased following the decisional step 122. The kV is increased in proportion to the mA ratio raised to the ¼ power in order to keep the film darkening factor constant. If this technique factor falls within the tube rating chart, then an exposure can be made in accordance with steps 110, 112, and 114. Otherwise, the entire process is repeated until the decisional step 122 indicates that the limit of the kV shift has been exhausted for the tube chart of first priority, e.g. small focal spot, standard speed. At this point the program has determined that exposure is not possible with the first priority rating chart, so the next desirable rating chart, e.g. small focal spot, ultra speed operation is chosen per step 124 with the process repeated until all tube charts going from the most desirable to the least desirable large focal spot, ultra speed, have been tried. According to decisional step 126, if all the tube charts have been tried and no exposure is possible, step 128 will provide an indication and/or prevent further operation of the system until a new set of technique factors have been inputted to the system per step 102. When desirable, a conscious overriding of this system by the operator in emergency cases is permitted.

Thus once having a set of operator selected technique factors inputted to the system, the program as shown in FIG. 5 begins by assuming the largest value of mA which is available from the generator, and then calculates the corresponding value of minimum exposure possible time. These values are then compared with the tube loading chart of first choice. If the factors are consistent with the tube loading chart, it takes the necessary steps to permit exposure. If the tube loading chart is exceeded, then the program directs modification to the first proposed set of technique factors such that if the calculated minimum exposure time corresponding to the maximum mA is less than some maximum allowable value which is stored in the program (or entered by the user) for preventing motion blurring, then a shift in factors is performed in such a way as to keep the mAs product constant by decreasing the mA and increasing the time by a prescribed amount. The new shifted technique factors of mA and time are now compared with the tube chart to see whether or not exposure can now be made. If exposure still cannot be made because the tube chart is exceeded, another reduction in mA with a corresponding increase in time is attempted provided the maximum time is not exceeded. After repeated shifts while maintaining a constant mAs, an alternate method is resorted to when the maximum motion blurring time is reached wherein reduction in mA and an increase in kV is now made while maintaining a constant film darkening factor. If the kV shift limit has not been exceeded, the program performs the kV shift by decreasing the mA, increasing the kV with the new set of parameters again compared with the tube chart. If a combination of constant mAs and kV shifts does not come up with a set of factors which will permit an exposure, then an exposure is not possible with the first tube loading chart, resulting in a move to the next most desirable tube chart with the process repeated and starting with the original factors inputted by the operator in hopes that exposure can be made. Successively then all the possible tube charts are stepped through in the order of desirability either until an allowable set of exposure factors is found, or it is determined that no exposure is possible within the constraints of the program.

Figure 6:
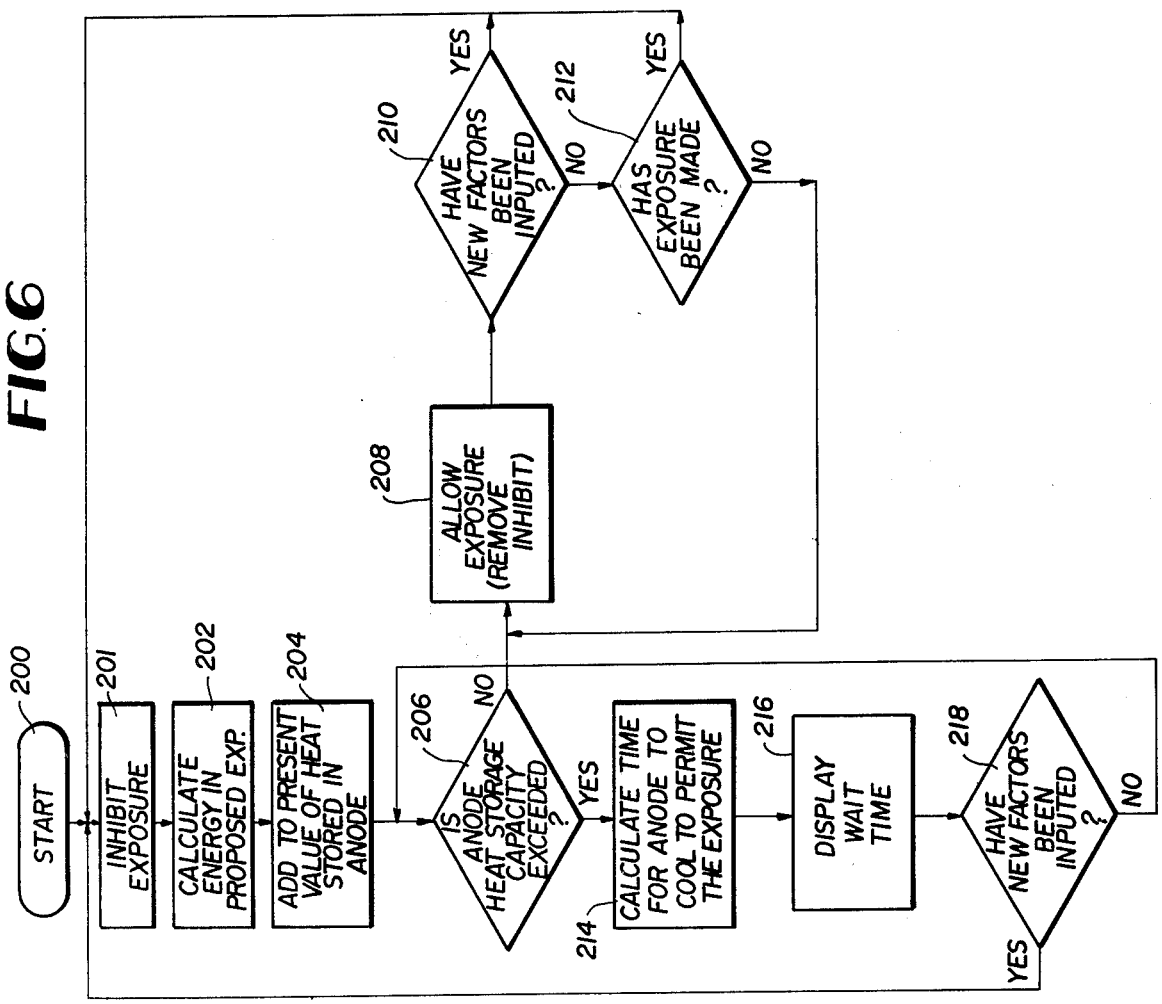

The microprocessor controlled X-ray generator according to the subject invention is adapted to provide additional functions from that set forth in FIG. 5, one of which, for example, is the verification of available anode heat capacity. Such an algorithm for the case of a single exposure is shown in FIG. 6. For purposes of illustration, it is assumed that this routine is embedded in the operating system which allows exposure unless it is inhibited. The system operation might be such that each time a new factor or factors are entered, this routine is called up. Since new factors have been entered, following the START step 200, exposure is first inhibited at step 201. At step 202 the energy in the proposed exposure is calculated which in step 204 is added to the value of heat already present in the anode from which a decisional step 206 is made to determine if the anode's heat storage capacity is exceeded. If it is not, a step 208 allows exposure by removing the inhibit, and the program passes on to two subsequent decisional steps 210 and 212, which inquire as to whether or not new factors have been inputted, and whether or not the present exposure has already been made. If the answer to both of these inquiries is NO, then step 208 is again initiated, continuing to permit exposure. If the answer is affirmative to any of the steps 210 and 212, the program reverts back to step 201. Note that being out of the exposure permitted loop, exposure is not permitted now. If the step 206 provides an affirmative decision meaning that the heat capacity is exceeded, a calculation step 214 is initiated wherein the time for cooling in order to permit the present exposure is made and the wait time is displayed at step 216. Note that at this point exposure inhibit of step 201 has not been disabled. A decisional step 218 is made following step 216 whereby if new factors have been inputted, the program reverts back to step 201, but on the other hand if a negative decision is rendered, steps 206, 214 and 216 are repeated until such new factors have been inputted to the system, or the decision 206 is negative indicating the tube anode has cooled enough to permit exposure. The value of the anode stored heat can be simulated by a digital or an analog circuit, or by a subroutine within the processor itself. Several alternate displays are also possible, such as the number of exposures of the proposed type which can be calculated, or the number of seconds of run permitted at a specified film speed for a photo-camera, or the number of seconds of a cine camera run which can be made consistent with the stored anode heat and heat capacity of the tube. Any or all of these calculations can be included in step 214, and the results displayed at 216.

Figure 7:
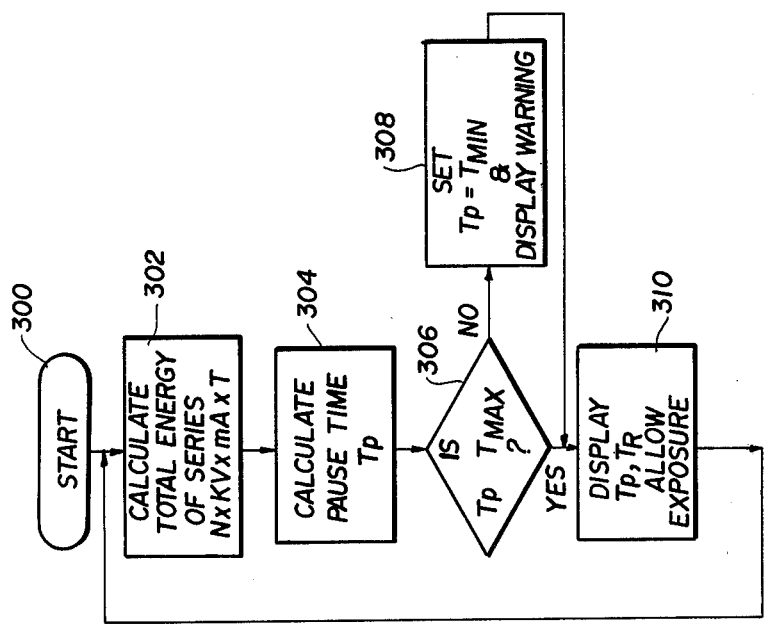

Reference to FIG. 7 indicates the algorithm for the calculation of the necessary wait time between successive exposures in a tomographic series. Based on the factors entered into the generator for each exposure and the number of exposures planned, the microprocessor 12 calculates the necessary wait time between successive exposures and in fact if desired, can automatically control the sequence of successive exposures. Referring to FIG. 7, following a START step 300, a calculation step 302 is carried out performing the multiplication of $N \times kV \times mA \times t$ where N is the number of films in the series. Next the pause time $T_p$ is calculated according to step 304 where $$T_p = \frac{\epsilon - (H_c - H_i)}{K(N - 1)} - (\frac{N}{N - 1}) \times T_{on}$$

where $\epsilon$ is the total energy in the series which is the result of the calculation shown in step 302, $H_c$ is the heat capacity of the housing, $H_i$ is the present value of the stored heat, which is continually corrected by other means such as an analog simulator of the anode stored heat or another program resident in the memory of the microprocessor, taking into account each exposure as it occurs and the continuous cooling of the X-ray tube, K is the housing cooling rate, and $T_{on}$ is the tomographic scan time or time of exposure.

Following the step 304, a decisional step 306 is entered into to determine if the pause time $T_p$ is greater than a required minimum waiting time of $T_{min}$. This minimum wait time is required for purposes relating to the clinical tomographic procedure, for example, the mechanical reset of the scanning apparatus, or allowing the patient to breathe and relax momentarily, etc. If the decision is negative, step 308 is entered into setting the wait time to the minimum and displaying a notice. If the decision of step 306 on the other hand is affirmative, step 310 is entered into wherein exposure is allowed while at the same time displaying the pause time $T_p$ and, when desired, the total series time $T_r$ which is equal to $NT_{on} + (N-1)T_p$. Following the exposure step 310, the process is repeated beginning with step 302 in order to permit recalculation if new factors have been entered, and to update the heat calculations.

The versatility of the subject invention is further displayed by the program set forth in FIG. 8, which is adapted to store X-ray tube history, that is a record of the usage of the X-ray tube(s) in terms of the number of exposures, the amount of energy applied to the anode, and the number of exposures under different sets of conditions. Starting with step 400, the flow chart in FIG. 8 begins with a decisional step as to whether or not a request has been made for a print-out of the tube history. If the answer is affirmative, then step 404 is entered into. If the answer is negative, a second decisional step 406 is initiated inquiring as to whether or not there has been an unfiled exposure. If the answer is yes, a series of instructions beginning with step 408 for example, commands the fetching of exposure data such as kV, mA, time, focal spot anode speed and tube number. Following this, the total number of exposure count for the appropriate tube is incremented according to step 410, followed by an incrementing step whereby the number of exposure counts for that tube at specified current focal spot and anode speed is made according to step 412. Following this, step 414 is entered into whereby the energy of exposure is calculated, which consists in multiplying the factors mA, kV, and time. Having made the calculation step 414, this energy of exposure is caused to be added to the total energy file for that tube and when desired, to send the result to an anode heat monitor program, not shown.

As was mentioned above, the subject invention is capable of being operated according to factors based upon an "anatomic table" wherein the operator chooses the selection of the anatomy to be X-rayed, the type of examination to be performed, the patient's type of physique. The microprocessor 10 and more particularly the PROM 34 is capable of and easily adapted to store and recall X-ray factors of an anatomic basis which leads to the flow chart shown in FIG. 9. This program requires an operator input by means of a set of pushbuttons, for example, specifying the anatomic part, technique, or view desired, patient thickness, and other qualifying factors, such as age. This patient information can, when desired, be inputted from an externally remote hospital computerized information system shown in FIG. 4. Following the START step 500, the step 502 indicates that the anatomic part and technique selection step initiates a read-out of the storage file for the proper kV and mAs following step 502. Also, qualifying factors such as thickness, age, etc. is inputted per step 506 and in accordance with these factors step 508 corrects the kV and/or mAs in accordance with the qualifying factors of step 506. This is consistent with contemporary or state of the art manual implementation where three patient levels, "thin", "medium" and "thick" are considered and accordingly the kV is raised by a fixed amount from a median if a patient is "thick" and reduced by a fixed amount if he is "thin". With a PROM a more complex algorithm can be provided for such compensation. Step 510 then stores data for statistical purposes followed by step 512 which sends the corrected kV and mAs factors to step 102 shown in FIG. 5, or equivalent.

Figure 10:
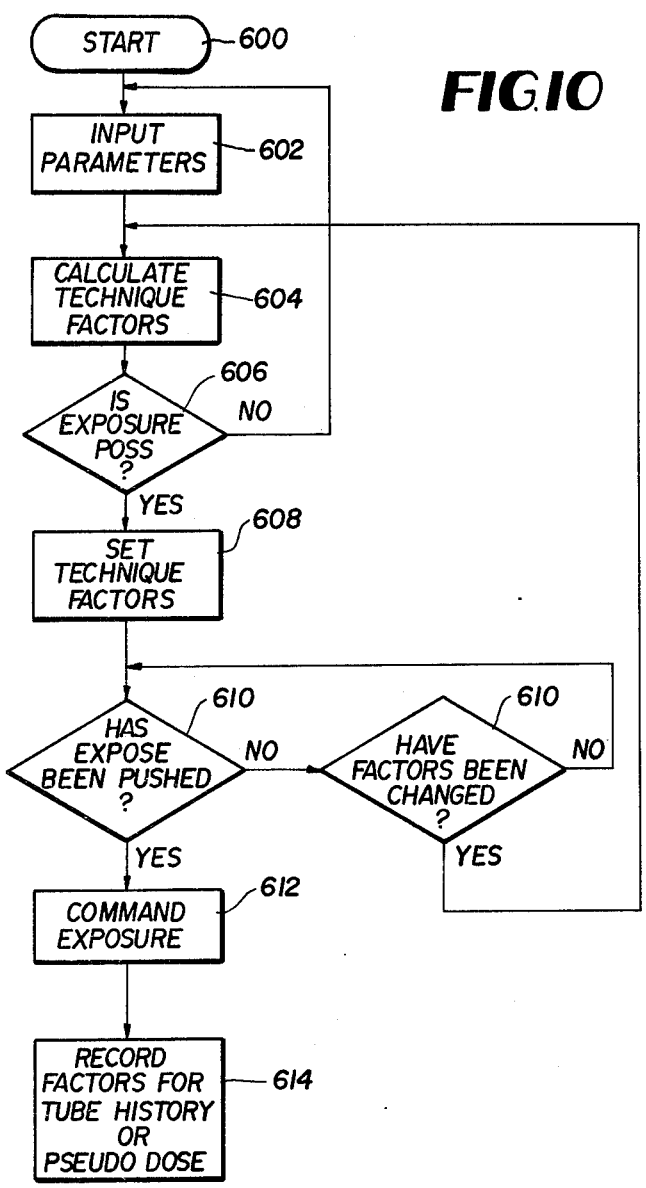

FIG. 10 discloses a generalized automatic operating program for the system shown in FIG. 4 and denotes that following a START step 600, input parameters are effected in steps 602, whereupon technique factors are next calculated in step 604 which may be in accordance with programs of the types in FIG. 5 and FIG. 8, following which a decision step 606 is made inquiring whether or not an exposure is possible.

The step 606 is very comprehensive and includes a variety of safety checks such as the anode heat monitoring program of FIG. 6, the tomographic series calculation of FIG. 7, and if, for example, a "tomo" procedure is at hand the other operating system checks which are needed, inter alia, to control the anode rotor drive circuits to assure that the anode is up to speed, monitor anode boost verification, check tube cooling status (e.g. cooling water flow) and film camera status (e.g., cassette loaded with film, motor running). These are all accomplished by subroutines like those illustrated or in some cases by interrupt signals to the microprocessor which identifies the cause for the interrupt and takes the necessary action ranging from signalling the operator to removing the cause for the interrupt in a satisfactory manner. If the decision is negative, then the program displays this fact and reverts back to step 602. However, if exposure is possible for the set of technique factors selected and entered per step 608, the proper signals are sent to the functional circuits 14, FIG. 4, whereupon a second decision step 610 inquires whether or not the exposure button has been pushed, which if an affirmative answer results, a command of exposure step 612 is initiated, followed by step 614, which records factors for tube history or other purposes such as a pseudo dose program shown in FIG. 11. If on the other hand the decision step 610 provides a negative answer, a question is again asked per step 616 whether any factors have been changed which if an affirmative answer is made, reverts back to step 604, while a negative step reverts back to the step 610.

Figure 11:
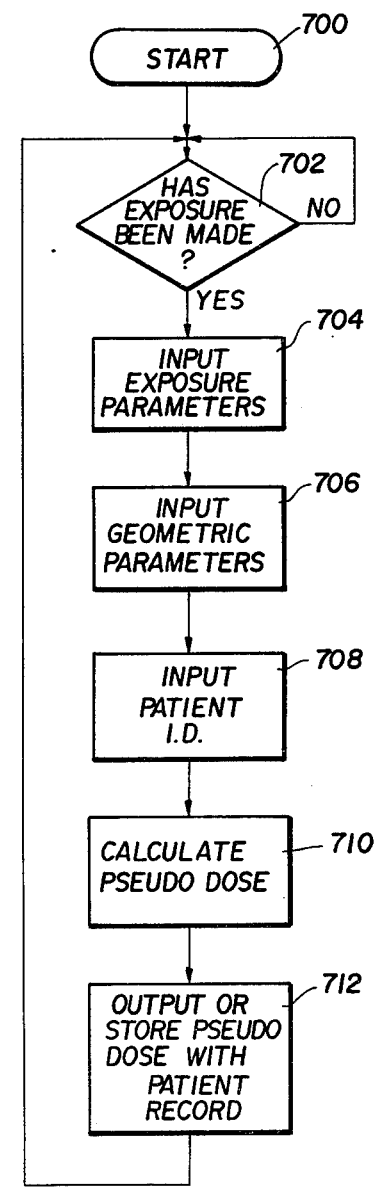

Finally, the flow chart of FIG. 11 is intended to illustrate a program wherein the patient dose of X-ray energy is estimated by a calculation based upon known and measured parameters, or, if a radiation sensor is employed such as the device 80 shown in FIG. 4, the calculation can be measured in part or in total. According to the flow chart in FIG. 11, following initiation step 700, a decisional step 702 inquires whether or not an exposure has been made. If the answer is affirmative, step 704 inputs exposure parameters such as kV, mA and time, whereupon geometric input parameters are next inputted per step 706, which input parameters consist of, for example, field size, source-image distance or source-object distances. Next, step 708 inputs patient identification followed by a calculation step 710, which is a pseudo dose calculation based upon the expression:

$$\text{pseudo dose} = \frac{A \times mA \times (\text{field size}) \times f(kV) \times \cos\theta}{(SOD)^2},$$

where $f(kV)$ is some function of kV which can be empirically determined, $\theta$ is the angle of incidence of the X-ray beam, and SOD is the source to object distance, and A is a constant depending on various physical parameters such as the age of the X-ray tube which are periodically determined and updated. Following this calculation, an output step 710 is initiated which is made available on some type of indicator, or the result is stored with other records of the patient maintained, for example, in a remote radiological department information system such as shown with reference numeral 22 shown in FIG. 4.

Thus what has been shown and described is a diagnostic X-ray control system utilizing a microprocessor which is adapted to automatically control the operation of an X-ray generator in accordance with one or more of a plurality of stored program instruction sets selectable upon demand to operate the generator more economically and in a fashion heretofore unobtainable. Having thus described what is at present considered to be the preferred embodiments of the invention, it will occur to those skilled in the art that various alterations, modifications, can be made without departing from the spirit and scope of the invention. Accordingly,

I claim:

1. A control system for diagnostic radiological apparatus, comprising, in combination:
   diagnostic radiological apparatus including a generator and control circuitry therefor operable in response to analog control signals applied thereto for producing radiological images according to a selected diagnostic procedure and including circuit means adapted to initiate processing operations of a stored program digital computer and to respond to said processing operations, said generator including at least one X-ray tube having a controllable focal spot and anode speed;
   a stored program digital computer including an interconnected central processing unit, memory and means for communicating with said radiological apparatus via said circuit means;
   a plurality of selectable instruction programs stored in said memory, each of said programs being adapted upon command to initiate predetermined control processing actions by said central processing unit, said central processing unit generating and coupling digital control signals to said means for communicating;
   said circuit means including interface circuit means, and including means for controlling the focal spot, anode speed of said X-ray tube, the voltage (kV) applied to said X-ray tube, the current (mA) drawn by said X-ray tube, and the exposure time (s) of at least one X-ray exposure by said X-ray tube and being responsive to said digital control signals to generate said analog control signals applied to said control circuitry and to be responsive to selected analog feedback signals from said radiological apparatus to generate digital signals coupled back to said stored program digital computer; and wherein
   said memory is programmed with binary information corresponding to tube rating chart curves for a plurality of focal spot sizes and anode speeds of said X-ray tube, and
   said circuit means includes means for supplying diagnostic procedural data including means for selecting technique factors comprising a combination of kV, mA and time.

2. The system as defined by claim 1 wherein said stored program digital computer comprises a microprocessor.

3. The system as defined by claim 1 wherein said memory comprises a read only memory.

4. The system as defined by claim 1 wherein said X-ray generator includes at least another tube having a controllable focal spot and anode speed and wherein said interface circuit means additionally includes means for selecting one of said X-ray tubes for a selected diagnostic procedure.

5. The system as defined by claim 1 wherein said memory is additionally digitally programmed with technique factors on an anatomic basis.

6. The system as defined by claim 1 wherein at least one of said instruction program comprises an instruction set for optimizing image quality and which is operable to: (a) determine the mAs product of inputted technique factors and using the highest value of mA which is available for said X-ray generator, calculate the corresponding minimum possible exposure time by dividing the maximum mA into the mAs product; (b) compare this combination of kV, mA and minimum exposure time against the parameters of the tube rating chart of first choice; (c) permit an exposure if within ratings; (d) if the tube rating chart of first choice is exceeded, direct modifications to the first proposal of inputted kV, mA and time technique factors in the following manner; (e) if the calculated minimum exposure time is less than a predetermined value which is established in order to minimize motion blurring, decrease mA and increase time proportionately, keeping the mAs product constant and again compare this combination against said tube rating chart of first choice, (f) permit an exposure if within rating, (g) if exposure is still not possible, repeat the mA downshift of (e) until the motion blurring time limit is reached, (h) maintain exposure time substantially constant, reduce mA and increase kV while maintaining a substantially constant film darkening effect, (i) compare this combination against said tube rating chart of first choice; (j) permit an exposure if within voltage, (k) if the combination of constant mAs and kV shifts does not provide a set of factors which will permit an exposure, (l) shift to the next most desirable tube rating chart and repeat (e) through (j) until an allowable set of exposure factors is found or all tube charts have been examined and no exposure can be made.

7. The system as defined by claim 1 wherein at least one of said instruction programs comprises an instruction set which is operable to: (a) calculate the heat energy in a proposed exposure; (b) add the value of the calculated heat energy to the value of the heat stored in the anode; (c) determine whether the anode heat storage capacity is exceeded; (d) allow exposure if the heat capacity is not exceeded; and (e) if the heat storage capacity is exceeded, calculate the time for the required anode cooling and inhibit exposure until the anode has cooled sufficiently, or a new acceptable set of technique factors has been entered.

8. The system as defined by claim 1 wherein at least one of said instruction programs comprises an instruction set which is operable to: (a) calculate the total energy in a tomographic series; and (b) calculate the required pause time between exposures and inhibit exposure unless the required pause time is ensured.

9. The system as defined by claim 1 wherein at least one of said instruction programs comprises an instruction set which is operable to: (a) store X-ray tube history in terms of the number of exposures; (b) store a record of the amount of energy applied to the anode; and (c) store a record of the number of exposures under different operating conditions; and (d) to output this information on command.

10. The system as defined by claim 1 wherein said at least one of said instruction programs comprises an instruction set which is operable to calculate and output a pseudo dose calculation of a predetermined patient.

11. The system as defined by claim 10 wherein said pseudo dose calculation is defined by the expression:

$$\text{pseudo dose} = \frac{A \times mA \times (\text{field size}) \times f(kV) \times \cos\theta}{(SOD)^2}$$

where A is a constant depending on certain physical parameters of said X-ray tube such as age, mA is the tube current to be inputted, field size is the size of the field of radiation to be applied to the object 1 patient, f(kV) is a predetermined function of the tube voltage to be inputted, $\theta$ is the angle of incidence of the X-ray beam to the subject, and SOD is the source to object 1 patient distance.

12. The system as defined by claim 1, wherein at least one of said instruction programs comprises an instruction set for optimizing image quality and is operable to: (a) calculate the minimum exposure time possible for the product of selected mA and exposure time, (b) compare the parameters of said minimum exposure time for the power resulting from said selected mA and kV with the parameters of a tube loading chart of first choice and permit an X-ray exposure if these parameters are within the allowable rating defined by said tube loading chart, (c) if said tube loading chart parameters are exceeded, effect a shifting of at least one technique factor consisting of mA, kV, and exposure time in a predetermined sequence and again make said comparison, and (d) in the event repetitive shifting of said at least one technique factor fails to permit an exposure, shift to the parameters of the next most desirable tube loading chart and repeat said comparison from the initial values and said shifting of said at least one technique factor, if necessary, until exposure is permissible, or all tube loading charts have been examined.

13. The system as defined by claim 12 wherein said shifting of said at least one technique factor includes a decrease in mA and an increase in exposure time while keeping kV and mAs substantially constant until the exposure time exceeds a value predetermined to prevent motion blurring.

14. The system as defined by claim 12 wherein said shifting of said at least one technique factor includes a decrease in mA and an increase in kV while maintaining substantially constant the film darkening capability of the technique factors.

15. The system as defined by claim 12 wherein said tube loading chart of first choice comprises the small focal spot, standard speed operating condition of said X-ray tube and wherein said next most desirable tube loading chart comprises the small focal spot, ultra speed condition and wherein the least most desirable tube loading chart comprises the large focal spot, ultra speed operating condition of said X-ray tube.

* * * * *